(12) United States Patent
Okada et al.

(10) Patent No.: US 10,798,291 B2
(45) Date of Patent: Oct. 6, 2020

(54) TASK-ASSISTANCE CONTROL APPARATUS AND TASK IMAGE CONTROL APPARATUS

(71) Applicant: OLYMPUS CORPORATION, Hachioji-shi, Tokyo (JP)

(72) Inventors: Keiji Okada, Tokyo (JP); Koji Sakai, Tokyo (JP); Reisuke Osada, Tokyo (JP); Mariko Ushio, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/422,222

(22) Filed: May 24, 2019

(65) Prior Publication Data
US 2019/0373164 A1  Dec. 5, 2019

(30) Foreign Application Priority Data
May 31, 2018 (JP) .................. 2018-104890

(51) Int. Cl.
H04N 5/232 (2006.01)
G06F 3/01 (2006.01)
H04N 7/18 (2006.01)

(52) U.S. Cl.
CPC ......... *H04N 5/23216* (2013.01); *G06F 3/013* (2013.01); *H04N 5/23203* (2013.01); *H04N 5/23296* (2013.01); *H04N 7/183* (2013.01)

(58) Field of Classification Search
None
See application file for complete search history.

(56) References Cited

U.S. PATENT DOCUMENTS

| | | | |
|---|---|---|---|
| 2015/0264299 A1* | 9/2015 | Leech ............... | H04N 21/6587 348/78 |
| 2016/0203602 A1* | 7/2016 | Hayashi ............. | A61B 1/00009 382/128 |

FOREIGN PATENT DOCUMENTS

JP          2016-143967 A     8/2016

* cited by examiner

*Primary Examiner* — Samira Monshi
(74) *Attorney, Agent, or Firm* — Volpe and Koenig, P.C.

(57) ABSTRACT

A task-assistance control apparatus that assists an operator performing a task while viewing a captured task image includes: a task-image acquisition circuit that acquires the task image; and a task determination circuit that determines task details on the basis of the type of a tool detected in the task image and the movement of the tool.

2 Claims, 22 Drawing Sheets

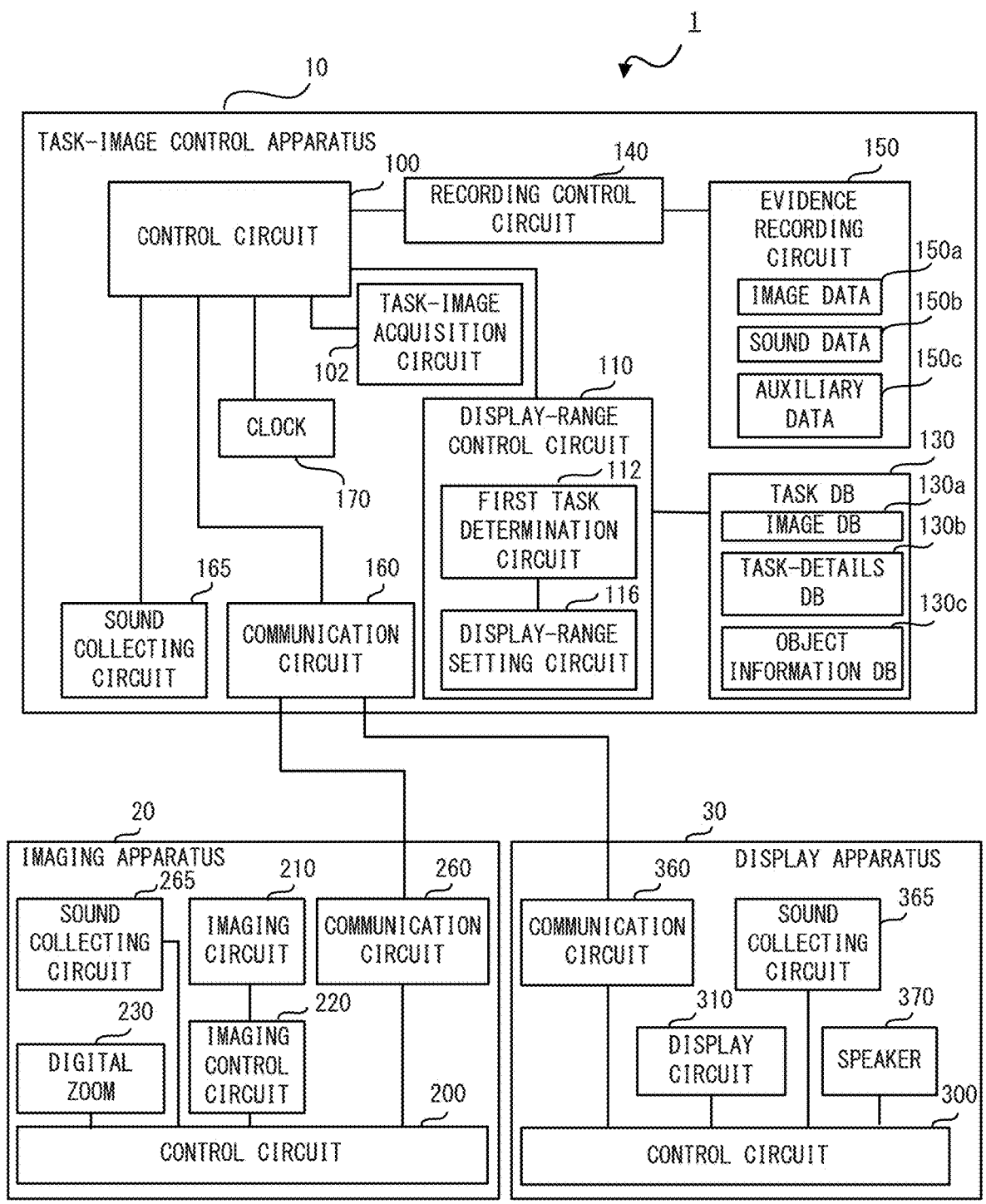
F I G. 1

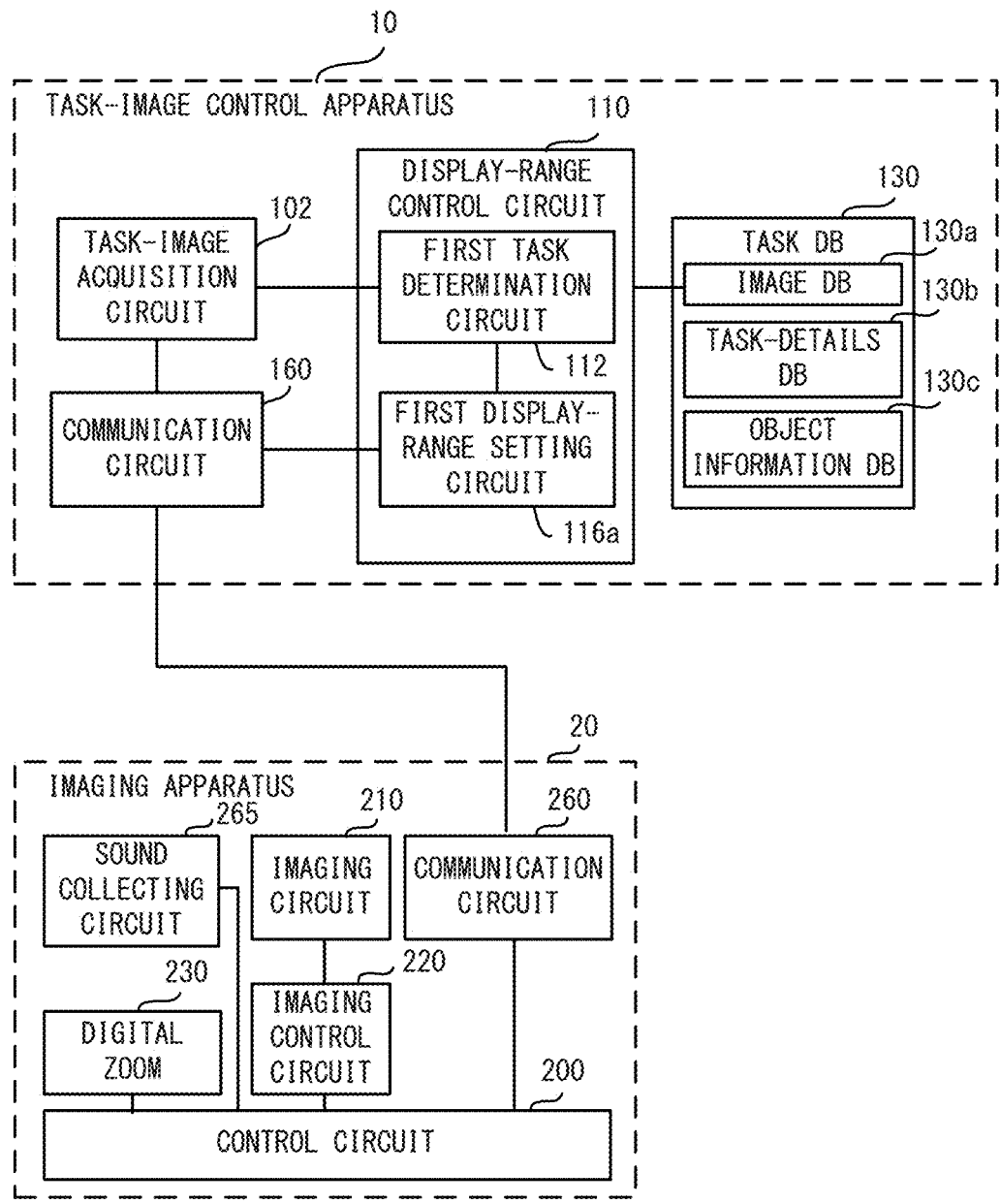
F I G. 3

EXAMPLE OF TASK-DETAILS DB

| TASK NAME | NAME OF TASK STEP | GUIDE INFORMATION | DETECTED INFORMATION | |
|---|---|---|---|---|
| | | | SCHEDULED TASK TIME PERIOD | USED TOOL |
| INSPECTION OF INTERNAL PART FOR FOREIGN BODY | PERFORATING AND INTERNAL OBSERVATION | SAMPLE IMAGE OF FOREIGN BODY | 10 MINUTES | DRILL |
| | REMOVAL OF FOREIGN BODY | SAMPLE IMAGE OF CUTTING OFF OF FOREIGN BODY | 10 MINUTES | PLIERS, CUTTER |
| | | | | |

F I G. 5

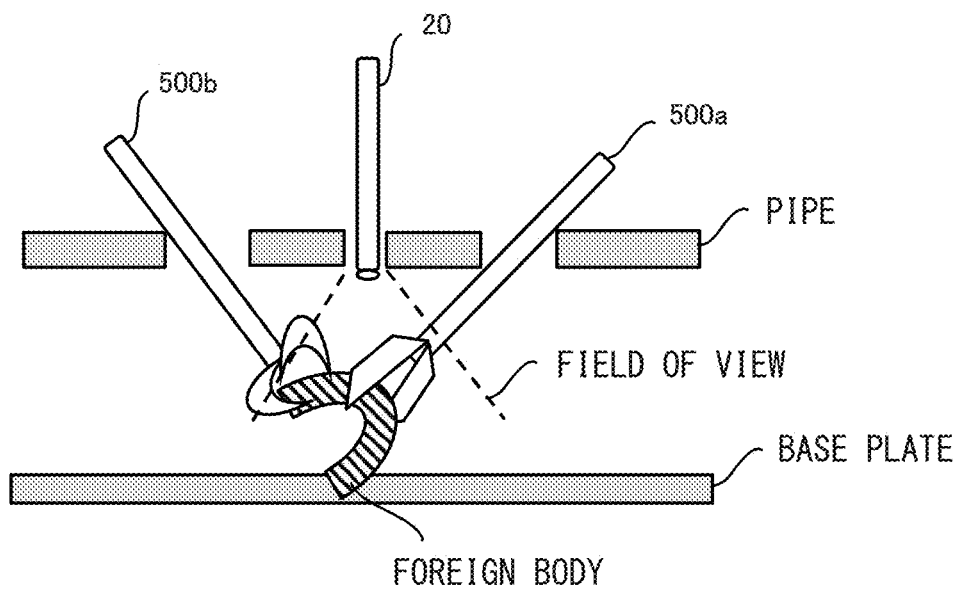
F I G. 7 A

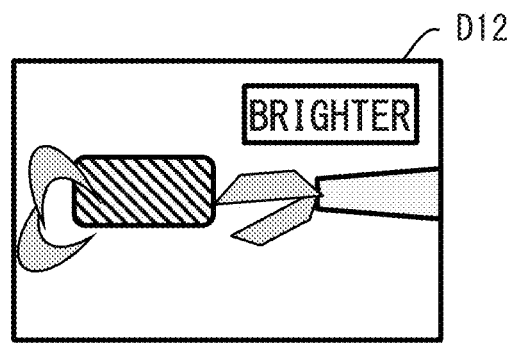
F I G. 8 C

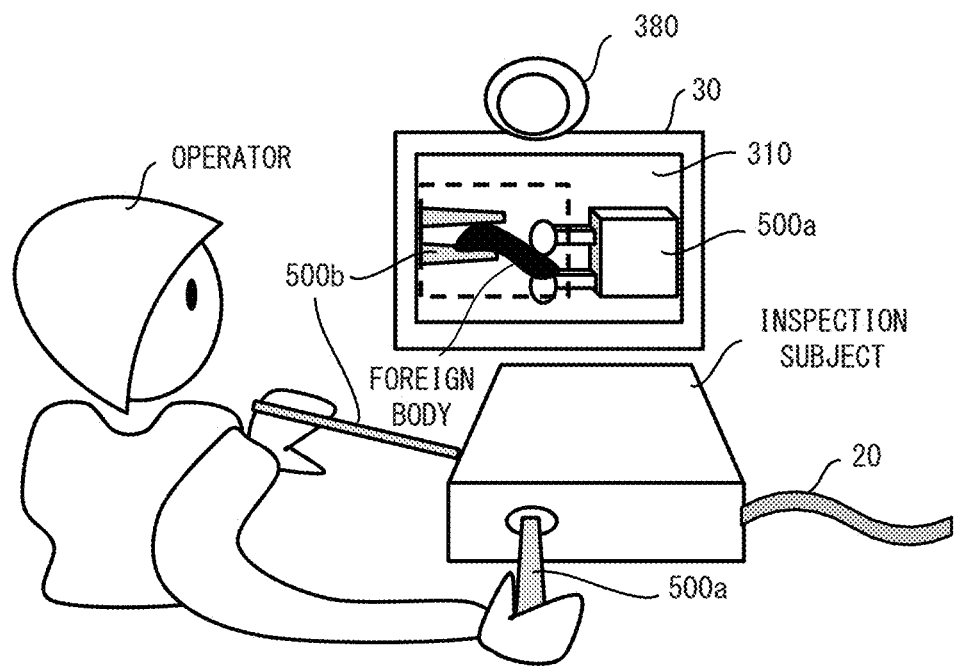
F I G. 12A

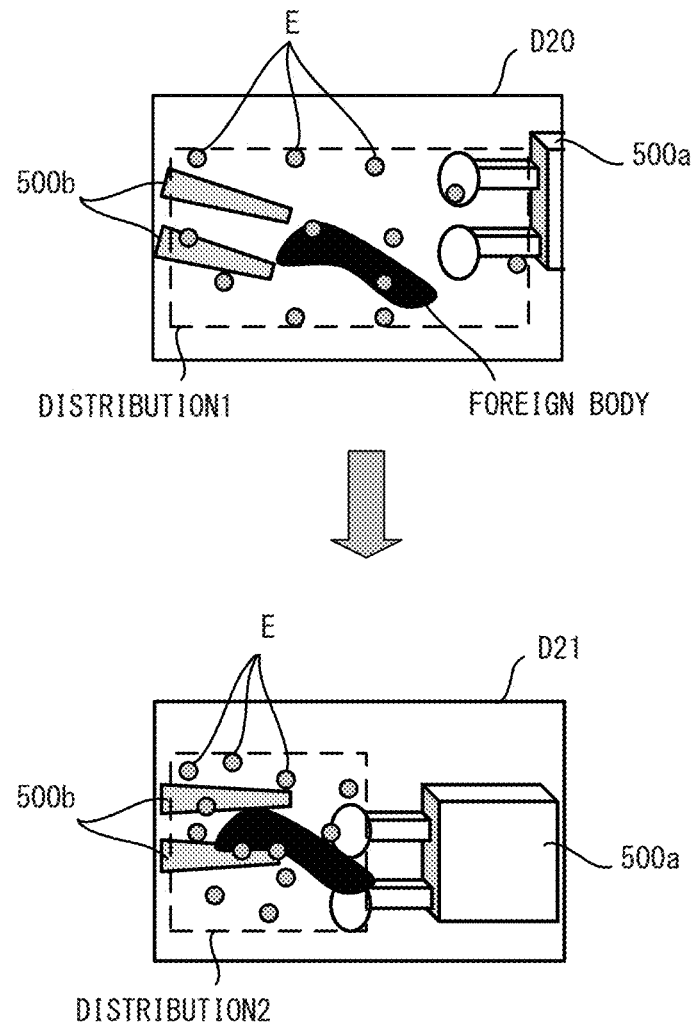
F I G. 13

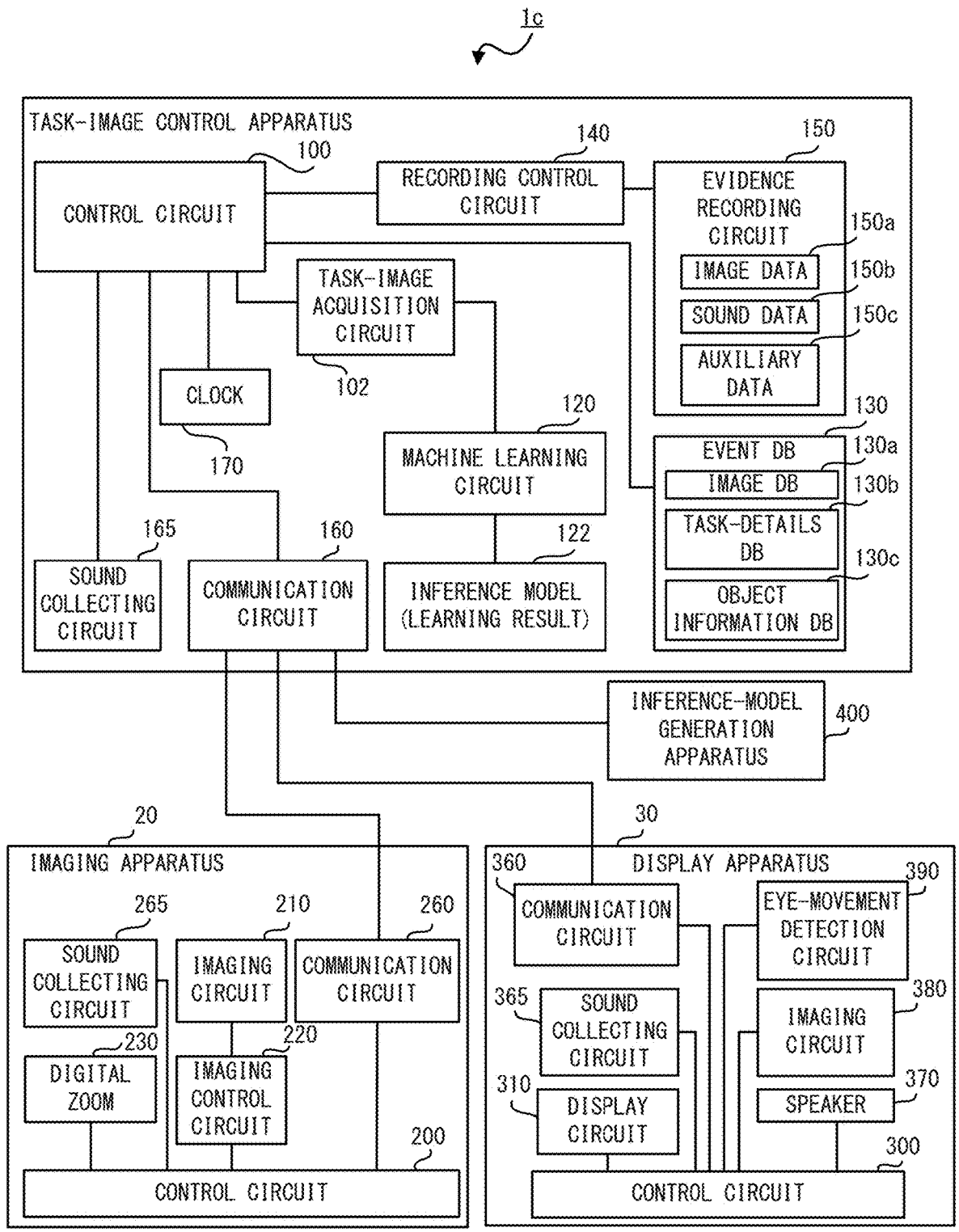
F I G. 14

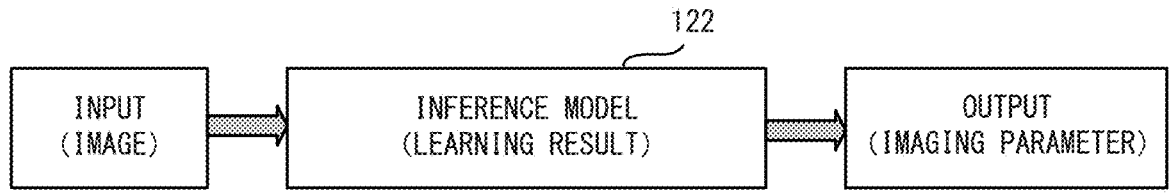
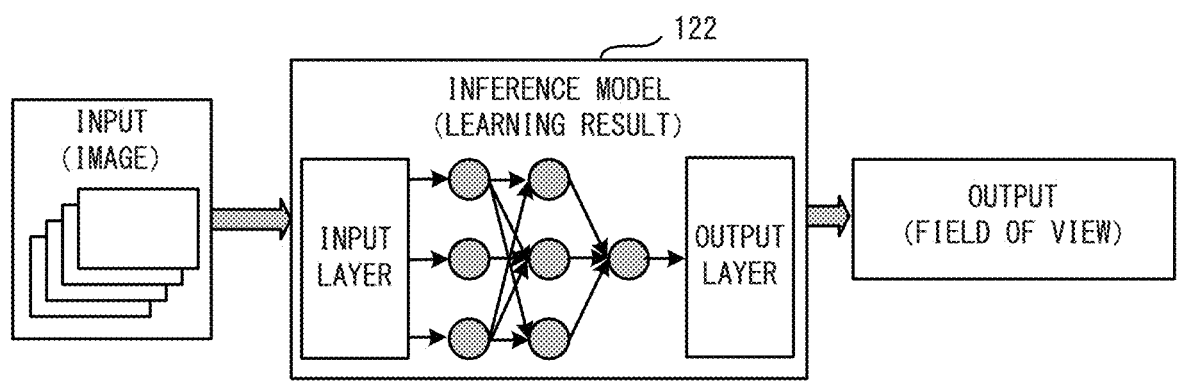
F I G. 17

TASK-ASSISTANCE CONTROL APPARATUS AND TASK IMAGE CONTROL APPARATUS

CROSS-REFERENCE TO RELATED APPLICATION

This application is based upon and claims the benefit of priority of the prior Japanese Patent Application No. 2018-104890, filed on May 31, 2018, the entire contents of which are incorporated herein by reference.

BACKGROUND OF THE INVENTION

Field of the Invention

The present invention relates to a technique pertaining to the fields of medical, biotechnology, and electronics in which an operator performs a detail-oriented task while viewing a real-time image and particularly relates to a task-assistance control apparatus and task-image control apparatus for appropriately setting a display range for an image while a task is performed.

Description of the Related Art

With the development of high-definition cameras and displays and the spread of high-speed communications, a task technique for performing a machine operation while viewing a real-time image has been utilized. A laparoscopic surgery is known in which an observation apparatus is inserted into the body (peritoneal cavity) and a surgery is performed while viewing an image on a monitor captured by the observation apparatus. Also, in the field of biotechnology, a sample or a material is processed (e.g., cut or peeled) by operating a manipulator apparatus while viewing a microscopic image on a monitor.

The capturing of such task images involves various types of image capturing assistance. This is because the image capturing range, brightness, and the like need to be optimized in accordance with the progress and details of the task in order to capture the task images. Proposed techniques for image capturing assistance include, for example, an imaging apparatus that detects and displays a camera posture on a screen as a guide so as to enhance the accuracy in image processing (Japanese Laid-open Patent Publication No. 2016-143967).

SUMMARY OF THE INVENTION

A task-assistance control apparatus in accordance with an aspect of the present invention that assists an operator performing a task while viewing a captured task image includes: a task-image acquisition circuit that acquires the task image; and a task determination circuit that determines task details on the basis of the type of a tool detected in the task image and the movement of the tool.

BRIEF DESCRIPTION OF THE DRAWINGS

The present invention will be more apparent from the following detailed description when the accompanying drawings are referenced.

FIG. 1 is an entire configuration diagram of a task-image control system;

FIG. 3 is a block diagram illustrating a first configuration of a display-range control circuit;

FIG. 5 illustrates a specific example of a table of a task DB;

FIG. 7A illustrates a specific example of the changing of a display range;

FIG. 8C illustrates an example of a screen for instructing a manipulator of an imaging apparatus to make an image "brighter";

FIG. 12A illustrates an example of the switching of a display range in accordance with a second embodiment;

FIG. 13 illustrates an example of the switching of a display range in accordance with a second embodiment;

FIG. 14 is an entire configuration diagram of a task-image control system in accordance with a third embodiment;

FIG. 17 models processing performed by a machine learning circuit in accordance with a third embodiment.

DESCRIPTION OF THE EMBODIMENTS

Figure 2:
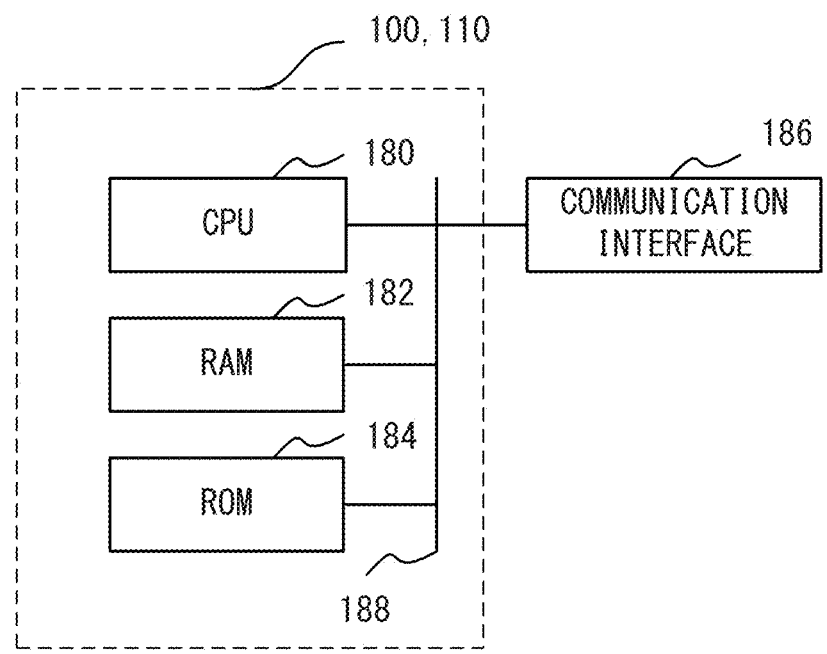
FIG. 2 is a hardware block diagram related to a control circuit and display-range control circuit of a task-image control apparatus.

The following describes embodiments of the present invention by referring to the drawings.

For example, hands-free controllable apparatuses are desired. Hence, it is desirable to provide a task-assistance control apparatus that can display an image appropriate for task details.

FIG. 1 is an entire configuration diagram of a task-image control system 1.

The task-image control system 1 displays in real time an image captured while a task is performed (this image may hereinafter be referred to as a task image) so as to assist an operator in performing the task while viewing the task image. The task-image control system 1 is utilized in a task performed for an internal portion that cannot be observed directly from outside. Tasks performed for internal portions are, for example, those performed in the fields of medical and biotechnologies and detail-oriented tasks performed for, for example, the inside of piping.

The task-image control system 1 includes a task-image control apparatus 10, an imaging apparatus 20, and a display apparatus 30. The task-image control apparatus 10 assists an operator in performing a task while viewing an image displayed in real time. The task-image control apparatus 10 provides the display apparatus 30 with an image suitable for the task by controlling a task-image range to be displayed on the display apparatus 30. In particular, the task-image control apparatus 10 determines task details and controls the size and direction of a displayed task image in accordance with the determined task details or a task-target portion. The task-image control system is also referred to as a task-assistance control system. The task-image control apparatus 10 is also referred to as a task-assistance control apparatus.

The task-image control apparatus 10 records images, sounds, and the like acquired by the imaging apparatus 20 as task evidence.

The task-image control apparatus 10 includes a control circuit 100, an image acquisition circuit 102, a display-range control circuit 110, a task DB 130, a recording control circuit 140, an evidence recording circuit 150, a communication circuit 160, a sound collecting circuit 165, and a clock 170.

The control circuit 100 performs centralized control of the entirety of the task-image control apparatus 10. The image acquisition circuit 102 acquires a task image from an external device, e.g., the imaging apparatus 20. The display-range control circuit 110 controls a task-image range to be displayed. The display-range control circuit 110 includes a first task determination circuit 112 and a display-range setting circuit 116.

The first task determination circuit 112 determines task details on the basis of, for example, a task image, a sound, or a task time period. The first task determination circuit 112 determines task details in accordance with, for example, the type of a tool 500 (industrial tool, surgical instrument) used within a task image or the movement of the tool 500. For example, the first task determination circuit 112 may detect a tool 500 through image processing of a task image and estimate the type of the tool by referring to an image DB 130a (this DB will be described hereinafter). Then, the first task determination circuit 112 compares the type of the tool 500 detected from the task image with the types of tools 500 scheduled to be used in various steps of the task so as to determine a task step that corresponds to this task image. Meanwhile, by referring to the movement or sound of the tool 500, the first task determination circuit 112 may determine a task step by making a comparison with a task-details DB 130b (this DB will be described hereinafter). The first task determination circuit 112 will also be described hereinafter by referring to FIG. 3.

In accordance with the task details determined by the first task determination circuit 112, the display-range setting circuit 116 sets an image range to be displayed. The display-range setting circuit 116 may use two different schemes: a scheme based on a first display-range setting circuit 116a and a scheme based on a second display-range setting circuit 116b. The display-range setting circuit 116 may include only one of the first display-range setting circuit 116a or the second display-range setting circuit 116b or may include both the first display-range setting circuit 116a and the second display-range setting circuit 116b and selectively use these circuits.

This configuration is effective even when a task image is not displayed, and can be used for a task check as to whether a task has been correctly performed or for creation of evidence. Accordingly, the task-assistance control apparatus can be one for displaying an image for a task as well as providing assistance in the task. An image range to be displayed and the way to display a guide or advice are required to be switched in accordance with the progress or details of a task. For example, just after a task is started, a wide range may be desirably displayed to check the entirety of a task subject, and in a later process of cutting a minute portion, an enlarged image of this portion may be desirably displayed.

Switching an image range involves manipulating the field of view of the camera or enlarging or reducing a display range. An operator typically manipulates a task tool with both hands and thus needs to temporarily stop the task in order to switch the field of view of the camera. The display-range setting circuit 116 allows an appropriate task image to be displayed in accordance with the progress of a task without the operator temporarily stopping the task.

The first display-range setting circuit 116a sets, in accordance with determined task details, a task-image range to be displayed and instructs the imaging apparatus 20 to change an image capturing range (angle or direction) in accordance with the task-image range that has been set. Details of the first display-range setting circuit 116a will be described hereinafter by referring to FIG. 3.

The second display-range setting circuit 116b sets, in accordance with determined task details, a task-image range to be displayed and extracts an image that falls within the task-image range from the task image so as to generate a task image to be displayed (the generated task image may hereinafter be referred to as a to-be-displayed task image). Details of the second display-range setting circuit 116b will be described hereinafter by referring to FIG. 4.

The task DB 130 is an accumulation of specific data collected in advance that relates to a task to be performed. When task details correspond to, for example, the removing of foreign bodies within a pipe, past data on the removal of foreign bodies within the pipe is stored by the task DB 130. The task DB 130 includes the image DB 130a, the task-details DB 130b, and object information 130c. The image DB 130a includes an image of a tool 500 (industrial tool, surgical instrument). The task-details DB 130b includes, for example, details and a schedule of a task to be performed. Object information 130c includes, for example, information on a subject for which a task (inspection) is to be performed.

FIG. 5 illustrates a specific example of a table of the task-details DB 130b. For example, the task-details DB 130b includes task name, task-step name, guide information, and detected information (scheduled task time period, used tool). When a task includes a plurality of processes, task-step name indicates the names of the steps of the task in order. Guide information indicates a sample of a task image for each task step. Scheduled task time period indicates an average period of time required to complete an individual task step. Used tool indicates the names of tools 500 to be used for individual task steps. Samples of task images and images of tools 500 are recorded by the image DB 130a.

This example is based on the assumption that the detecting is performed to determine what a tool is, and movement information of the tool may be added to the table. Accordingly, more accurate task assistance can be provided by additionally considering information on how the tool is actually used. In this case, as will be described hereinafter, the operator's eye movement may be detected to provide the table further in consideration of information on which portion of a task image the operator watched.

The recording control circuit 140 records, for example, task images, sounds generated in the task, and periods of actual task times required for individual task steps (task evidence) in the evidence recording circuit 150. Image data 150a, sound data 150b, and auxiliary data 150c are recorded by the evidence recording circuit 150. Voice instructions may be given to the machine via speech recognition so that information on what the operator said in that situation can be reflected in the table depicted in FIG. 5.

For example, task images may be recorded as image data 150a. The task images may be moving images, still images, or both moving images and still images. Sounds generated during a task are recorded as sound data 150b. The sounds are the operator's or an assistant's voice. The sounds may be those collected by any of the task-image control apparatus 10, the imaging apparatus 20, and the display apparatus 30. The periods of actual task times required for individual task steps, the operator's comments, and the like are recorded as auxiliary data 150c.

The communication circuit 160 controls transmission and reception of various data between the task-image control apparatus 10 and the imaging apparatus 20 and display apparatus 30. The communication scheme based on the communication circuit 160 may be directed to both a cable communication and a radio communication. The sound collecting circuit 165 includes a microphone to collect sounds. The clock 170 reports time information to the control circuit 100.

The imaging apparatus 20 includes a control circuit 200, an imaging circuit 210, an imaging control circuit 220, a digital-zoom processing circuit 230, a communication circuit 260, and a sound collecting circuit 265. The control circuit 200 performs centralized control of the entirety of the imaging apparatus 20 through software processing performed by, for example, a central processing unit (CPU). The imaging circuit 210 includes, for example, a lens circuit, a lens driving circuit, and an imaging processing circuit and generates a captured image.

The imaging control circuit 220 controls the lens driving circuit so as to control, for example, a focal length, a focal position, a diaphragm, and a shutter speed. The imaging control circuit 220 controls, for example, the focal length (field of view) in response to not only an input operation performed using an operation circuit provided at the imaging apparatus 20 but also an instruction from the task-image control apparatus 10 given via the communication circuit 260. Accordingly, when the imaging apparatus 20 has received an instruction to change (enlarge, reduce) an image capturing range from the first display-range setting circuit 116a of the task-image control apparatus 10, the imaging control circuit 220 changes the field of view (focal length) in accordance with this instruction.

The digital-zoom processing circuit 230 extracts a portion of an image and generates an enlarged image of this portion. Upon receipt of an instruction to change the size or position of an image capturing range from the task-image control apparatus 10, the digital-zoom processing circuit 230 extracts a portion of an image and generates an image of this portion in accordance with this instruction. The generated image is transmitted to the task-image control apparatus 10 as a task image.

In accordance with the change instruction from the task-image control apparatus 10, the imaging apparatus 20 may choose to use only either of optical zoom processing based on the imaging control circuit 220 or processing based on the digital-zoom processing circuit 230 or may choose to use a combination of these two types of processing. Accordingly, the lens circuit may always be set to a wide field of view, and the size or position of the image capturing range may be changed through digital zoom processing. This image may be used for a check by the operator or may be displayed to be checked by a supervisor at a distant place. This image can still be effective even when being simply recorded as evidence without being displayed.

The task-image control apparatus 10 may directly instruct the imaging apparatus 20 to set a certain field of view and an extraction range associated with digital zooming. Alternatively, the task-image control apparatus 10 may send an instruction to change the size or position of the image capturing range to the imaging apparatus 20, and the control circuit 200 of the imaging apparatus 20 may calculate the size of the field of view and conditions for digital zooming in accordance with the instruction so as to control the imaging control circuit 220 and the digital-zoom processing circuit 230, thereby changing the image capturing range.

The communication circuit 260 controls transmission and reception of data between the imaging apparatus 20 and the task-image control apparatus 10. The sound collecting circuit 265 has a microphone installed therein to collect sounds. The control circuit 200 captures a moving image or a still image. The control circuit 200 combines sounds with the moving image. The control circuit 200 transmits such a captured image to the task-image control apparatus 10 as a task image.

The display apparatus 30 includes a control circuit 300, a display circuit 310, a communication circuit 360, a sound collecting circuit 365, and a speaker 370. The control circuit 300 performs centralized control of the entirety of the display apparatus 30 through software processing performed by, for example, a CPU. The display circuit 310 is a display device such as an LCD to display a task image.

The communication circuit 360 controls a communication between the display apparatus 30 and the task-image control apparatus 10. The sound collecting circuit 365 has a microphone installed therein to collect sounds. The speaker 370 outputs, for example, sounds for moving images. The communication circuit 260 of the imaging apparatus 20 and the communication circuit 360 of the display apparatus 30 may be communicably connected to each other.

FIG. 2 is a hardware block diagram related to the control circuit 100 and display-range control circuit 110 of the task-image control apparatus 10. The task-image control apparatus 10 includes a CPU 180, a RAM 182, a ROM 184, a communication interface 186, and a bus 188.

The CPU (central processing unit) 180 reads a control program from the ROM 184 and performs various control processes through software processing based on this control program. The RAM 182 is a work area for temporarily storing a control program or various data such as captured images. The RAM 182 is, for example, a dynamic random access memory (DRAM).

The ROM 184 is a nonvolatile storage apparatus that stores, for example, control programs and various data. The ROM 184 is, for example, a hard disk drive (HDD) or a flash memory. The ROM 184 implements the task DB 130 and the evidence recording circuit 150. The ROM 184 also stores an operation guide for an operator. The operation guide will be described hereinafter by referring to FIG. 9. The CPU 180 is connected to, for example, the RAM 182 and the ROM 184 by a bus 188. The communication interface 186 implements the communication circuit 160.

FIG. 3 is a block diagram illustrating a first configuration of the display-range control circuit 110. The first configuration is such that the display-range setting circuit 116 is the first display-range setting circuit 116a.

The image acquisition circuit 102 acquires a task image via the communication circuit 160. The first task determination circuit 112 determines task details in accordance with, for example, the type of a tool 500 (industrial tool, surgical instrument) used within the task image or the movement of the tool 500 within the task image. For example, the first task determination circuit 112 may refer to the image DB 130a so as to determine task details and the type of a tool 500 (industrial tool, surgical instrument) used within the task image.

The first display-range setting circuit 116a sets, in accordance with determined task details, a task-image range to be displayed and instructs the imaging apparatus 20 to change an image capturing range. The image-capturing-range change instruction from the first display-range setting circuit 116a is transmitted to the imaging apparatus 20 via the communication circuit 160.

The image-capturing-range change instruction is received via the communication circuit 260 of the imaging apparatus 20 and reported to the control circuit 200. The control circuit 200 reports the image-capturing-range change instruction to the imaging control circuit 220 and the digital-zoom processing circuit 230. For example, the imaging control circuit 220 may change the field of view of the imaging circuit 210 in accordance with the image-capturing-range change instruction. In particular, when the image-capturing-range change instruction is an instruction to reduce the image capturing range (i.e., an instruction to enlarge an image of a portion of the subject), the imaging control circuit 220 performs control to narrow the field of view of the imaging circuit 210. The digital-zoom processing circuit 230 may extract an image for a position or range that corresponds to the image-capturing-range change instruction.

Figure 4:
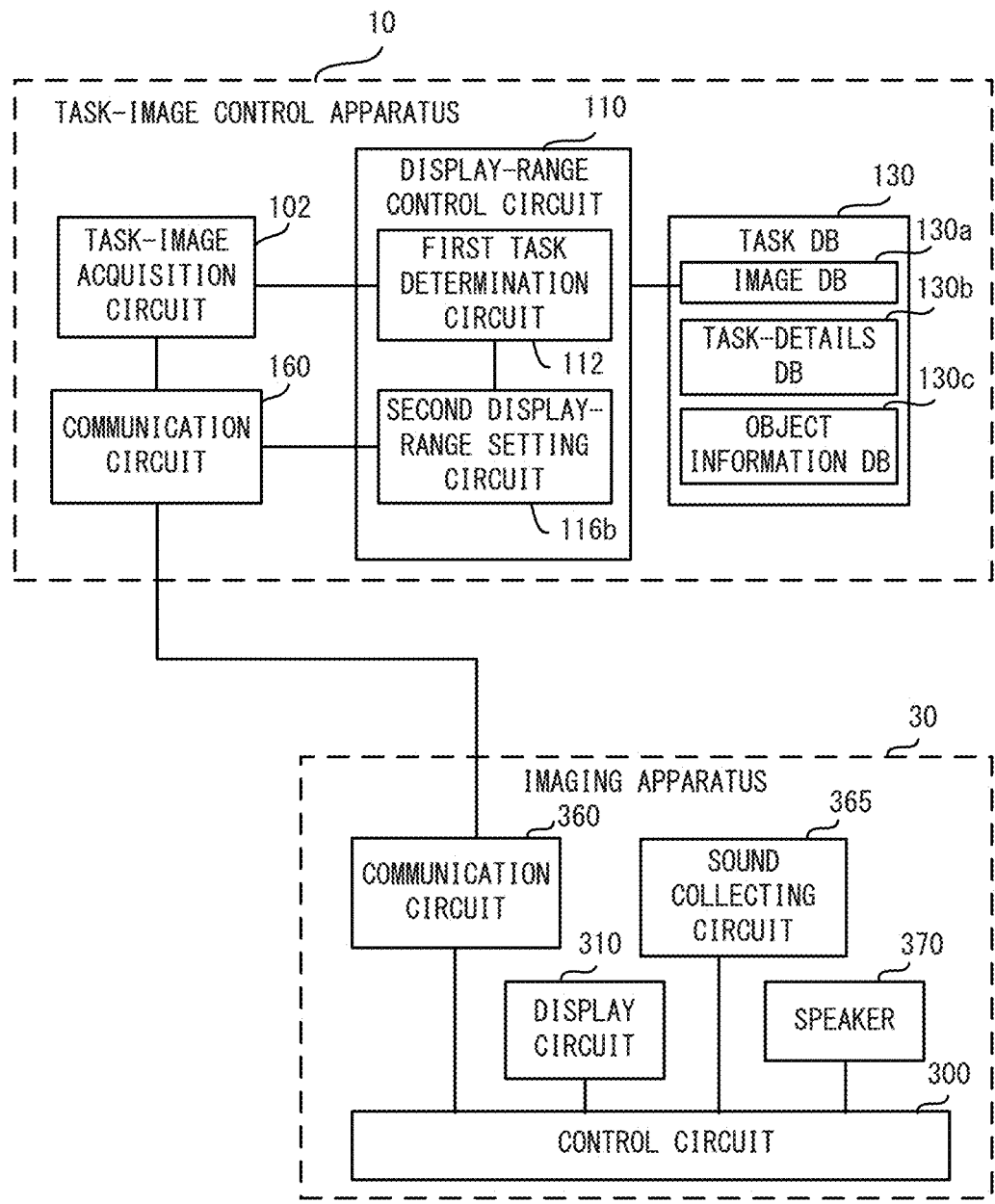
FIG. 4 is a block diagram illustrating a second configuration of a display-range control circuit.

FIG. 4 is a block diagram illustrating a second configuration of the display-range control circuit 110. The second configuration is such that the display-range setting circuit 116 is the second display-range setting circuit 116b. As described above, the second display-range setting circuit 116b sets, in accordance with determined task details, a task-image range to be displayed. Then, the second display-range setting circuit 116b extracts an image that falls within the task-image range from an image captured by the imaging apparatus 20 so as to generate a to-be-displayed task image. The processing performed by the second display-range setting circuit 116b is equivalent to the processing performed by the digital-zoom processing circuit 230. The task-image control apparatus 10 outputs the generated to-be-displayed task image from the communication circuit 160 to the display apparatus 30. The display apparatus 30 displays the to-be-displayed task image on the display circuit 310.

Figure 6A:
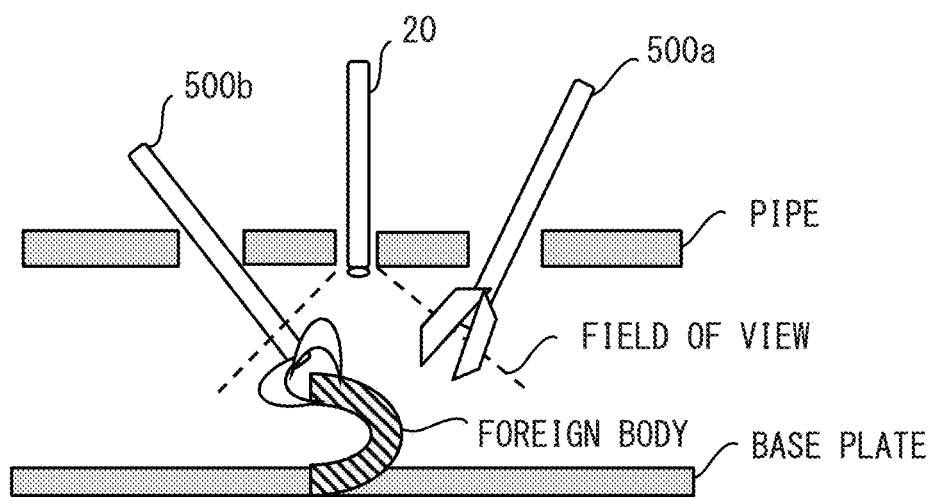
FIG. 6A illustrates a specific example of the changing of a display range.
Figure 6B:
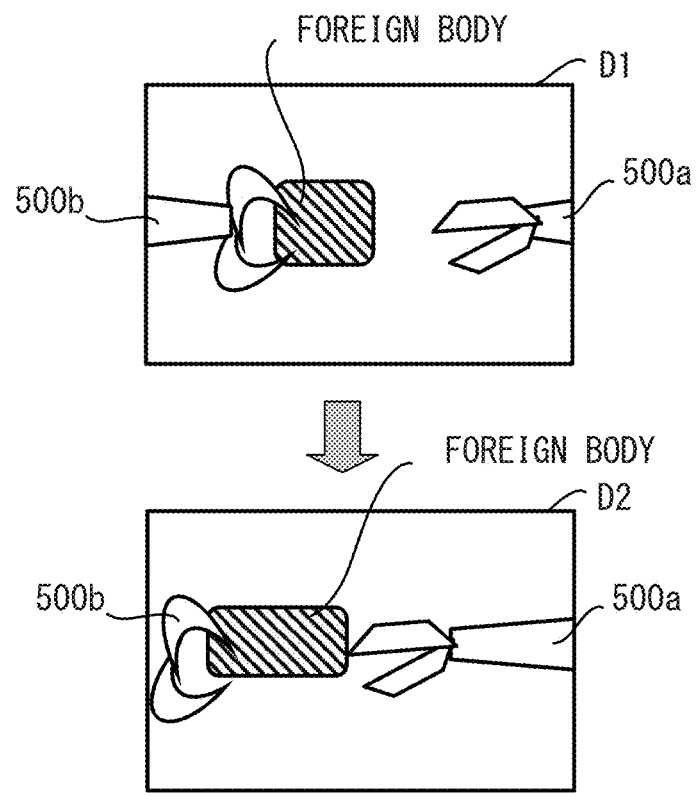
FIG. 6B illustrates a specific example of the changing of a display range.
Figure 7B:
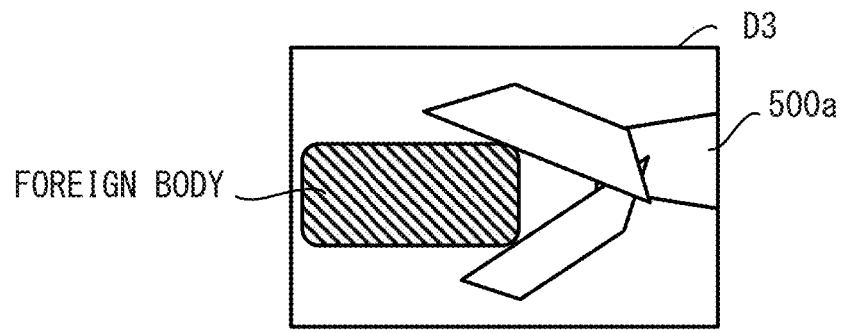
FIG. 7B illustrates a specific example of the changing of a display range.

FIGS. 6A, 6B, 7A, and 7B each specifically depict how a display range is changed. FIGS. 6A and 7A are each a cross-sectional view of a pipe under inspection. An inspection subject is a pipe in which a base plate is disposed. FIG. 6A indicates a situation in which after the pipe is perforated, a leading edge of the imaging apparatus 20, a cutter 500a, and pliers 500b are inserted into the pipe, and the pliers 500b holds a foreign body on the internal base plate.

FIG. 6B depicts an image of the task indicated in FIG. 6A. Image D1 indicates a situation in which the pliers 500b hold the foreign body. Image D2 indicates a situation in which the foreign body held by the pliers 500b has been taken off from the base board and is about to be cut by the cutter 500a. For the tasks up to the task of the pliers 500b firmly holding the foreign body, not only the foreign body but also the surroundings thereof are desirably indicated within the screen.

FIG. 7A is a cross-sectional view of the pipe during the task of cutting off the foreign body. The task of cutting off the foreign body is such that the operator cuts off the foreign body by moving the cutter 500a to a cut-off position on the foreign body. In this task, an enlarged image of the foreign body is desirably displayed so that the cutter 500a can cut off the foreign body at an accurate position. Accordingly, the first task determination circuit 112 refers to the image DB 130a and the task-details DB 130b so as to determine that the pliers 500b has caught the foreign body (image D2 in FIG. 6B). Then, by referring to the image DB 130a and the task-details DB 130b, the display-range setting circuit 116 sets a range of "foreign body and cutter 500a" as an image range to be displayed.

When the display-range setting circuit 116 is the first display-range setting circuit 116a, the imaging apparatus 20 is instructed to change the image capturing range (field of view and/or direction) in accordance with the range of "foreign body and cutter 500a" that has been set. When the display-range setting circuit 116 is the second display-range setting circuit 116b, a range corresponding to the range of "foreign body and cutter 500a" that has been set is extracted from a captured image so as to generate a to-be-displayed task image. An image D3 depicted in FIG. 7B is an exemplary image displayed by the display circuit 310. In particular, the image D3 is an enlarged image of the foreign body and the leading edge of the cutter 500a. The enlarged image is important for confirmation in the task process and the checking process.

When the imaging apparatus 20 is manipulated by a manipulator, not an operator, the display-range setting circuit 116 may indicate a task-image range that has been set to the manipulator of the imaging apparatus 20. The manipulator of the imaging apparatus 20 may be referred to as a scopist. The display-range setting circuit 116 includes a manipulator guide circuit 116c to guide the manipulator on how to manipulate the imaging apparatus 20.

Figure 8A:
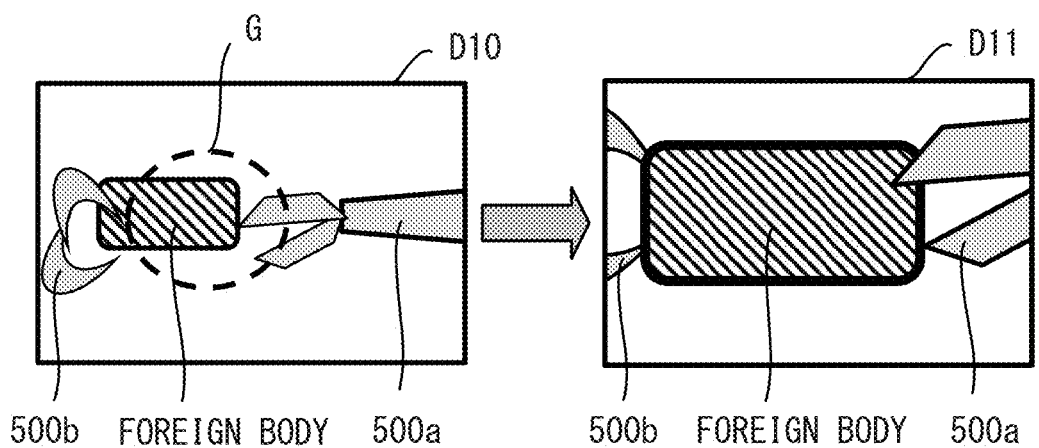
FIG. 8A illustrates an example of a screen for instructing a manipulator of an imaging apparatus to enlarge an image.
Figure 8B:
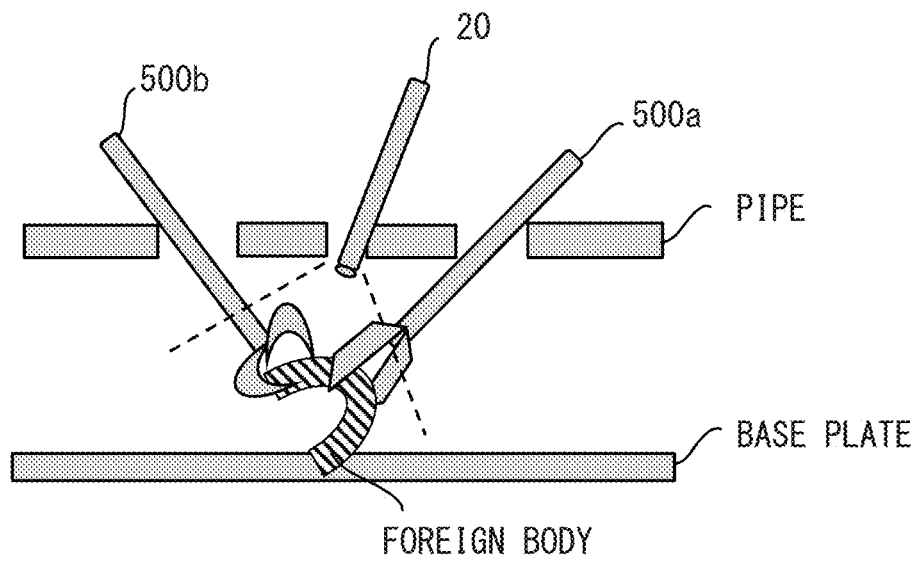
FIG. 8B illustrates an example of a screen for instructing a manipulator of an imaging apparatus to enlarge an image.

FIGS. 8A, 8B, and 8C are each an explanatory diagram for an example of processing based on the manipulator guide circuit 116c. FIGS. 8A and 8B each illustrate an example of a screen for instructing the manipulator of the imaging apparatus 20 to enlarge an image. An image D10 depicted in FIG. 8A indicates a condition in which an operator has taken a foreign body held by the pliers 500b off from a base plate and is about to cut this foreign body with the cutter 500a. This is similar to the condition indicated by the image D2 in FIG. 6B.

When the first task determination circuit 112 has determined this condition, the manipulator guide circuit 116c displays a guide G on the screen as a range to be enlarged. As indicated by the image D10 in FIG. 8A, the guide G, which is represented by a broken line, is displayed to essentially surround the foreign body.

The condition depicted in FIG. 8B is such that the manipulator who saw image D10 has changed the direction and field of view of the imaging apparatus 20 in order to have an enlarged image of the foreign body displayed. An image D11 depicted in FIG. 8A is an image of the foreign body that is captured under the condition indicated in FIG. 8B. The image D11 is also an enlarged image of the foreign body.

Not only a task-image range but also a desirable change to be made in image-shooting conditions may be indicated on the screen. In particular, the first task determination circuit 112 may determine image-shooting conditions in accordance with task details, and the manipulator guide circuit 116c may indicate a desirable change to be made in the image-shooting conditions on the screen. The image D12 depicted in FIG. 8C is an example of a screen for giving the manipulator of the imaging apparatus 20 an instruction to make the image "brighter" as a manipulator guide. Upon seeing this screen, the manipulator of the imaging apparatus 20, for example, opens the diaphragm of the imaging apparatus 20.

The manipulator guide circuit 116*c* allows the manipulator of the imaging apparatus 20 to adjust the image capturing direction and field of view of the imaging apparatus 20 on the basis of an instruction indicated on the screen, and hence the operator does not need to give an instruction to the manipulator and thus can concentrate on the task. Instructions can be reliably given even in a task environment where a verbal instruction is difficult to be given to the manipulator of the imaging apparatus 20. Even if the manipulator of the imaging apparatus is unaccustomed to performing the task, the task can be progressed without a major problem. Moreover, the manipulator guide circuit 116*c* eliminates the need for the imaging apparatus 20 and the display apparatus 30 to be controlled by the task-image control apparatus 10.

Figure 9:
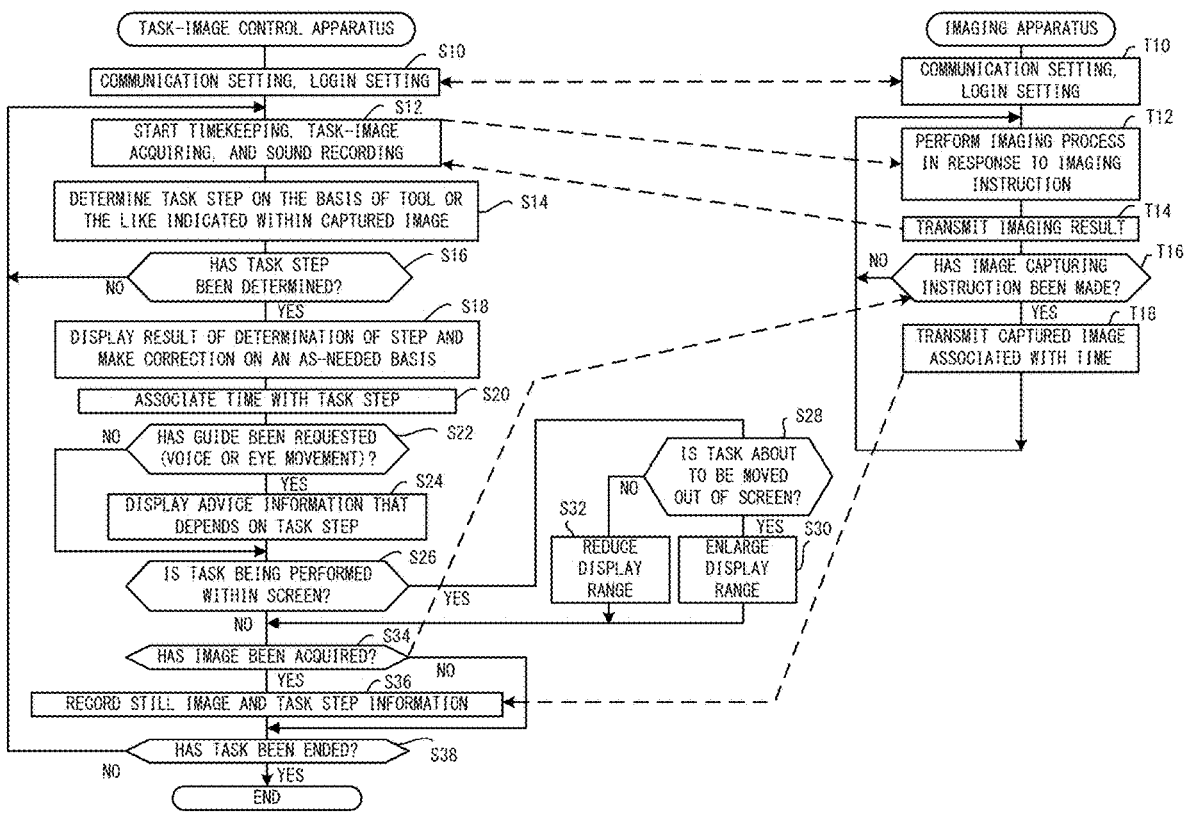
FIG. 9 is a flowchart illustrating the procedure of a task-image control process.

FIG. 9 is a flowchart illustrating the procedure of a task-image control process. The task-image control apparatus 10 makes a communication setting for the imaging apparatus 20 and performs a login setting (step S10). In response to this, the imaging apparatus 20 makes a communication setting for the task-image control apparatus 10 and performs a login setting (step T10).

The control circuit 100 of the task-image control apparatus 10 starts timekeeping, task-image acquiring, and sound recording (step S12). In response to an imaging instruction from the task-image control apparatus 10, the imaging apparatus 20 performs an imaging process for a moving image (step T12) and transmits an imaging result (a moving image with sounds) as a task image (step T14).

The image acquisition circuit 102 of the task-image control apparatus 10 acquires a task image (imaging result) transmitted from the imaging apparatus 20. The control circuit 100 outputs the task image to the display apparatus 30, and the task image is displayed on the display circuit 310 of the display apparatus 30. The imaging apparatus 20 waits for a still-image capturing instruction from the task-image control apparatus 10 (step T16).

The first task determination circuit 112 determines a task step on the basis of, for example, the type and operation of a used tool indicated within the captured image (this may include time and sound) (step S14). The control circuit 100 decides whether the task step has been determined (step S16). Upon deciding that the task step has not been determined (NO in step S16), the control circuit 100 returns to step S12.

Upon deciding that the task step has been determined (YES in step S16), the control circuit 100 displays a result of the determination of the task step and makes a correction on an as-needed basis (step S18). The operator inputs a correction when the displayed task step is incorrect.

The control circuit 100 associates a time and the task step with each other (step S20). The control circuit 100 decides whether the operator has made a request to display advice by voice or eye movement (step S22). The advice refers to task advice to be given to the operator (e.g., a procedure for the task, tools to be used, inspection method). For example, advice information may be stored in the ROM 184.

Upon deciding that the operator has made an advice request by voice or eye movement (YES in step S22), the control circuit 100 displays advice information that depends on the task step (step S24).

As will be described hereinafter by referring to a second embodiment, when the display apparatus 30 is provided with an imaging circuit for detecting eye movement, the control circuit 100 may decide according to a report from the display apparatus 30 whether the operator has made an advice request by eye movement. When, for example, the display apparatus 30 has sensed the operator watching an advice display icon displayed on the screen, the display apparatus 30 reports to the task-image control apparatus 10 that an advice request has been made. Upon deciding that the operator has not made an advice request by voice or eye movement (NO in step S22), the control circuit 100 shifts to step S26.

The first task determination circuit 112 decides whether the task (treatment) is being performed within the screen (step S26). Upon deciding that the task (treatment) is not being performed within the screen (NO in step S26), the first task determination circuit 112 shifts to step S34.

Upon deciding that the task is being performed within the screen (YES in step S26), the first task determination circuit 112 determines whether the task is about to be moved out of the screen (step S28). When the first task determination circuit 112 has determined that the task is about to be moved out of the screen (YES in step S28), the display-range setting circuit 116 sets an enlarged image range to be displayed (step S30). In particular, when the display-range setting circuit 116 is the first display-range setting circuit 116*a*, the imaging apparatus 20 is instructed to enlarge the field of view (shorten the focal length). When the display-range setting circuit 116 is the second display-range setting circuit 116*b*, a to-be-displayed task image is generated for a wide range.

When the first task determination circuit 112 has determined that the task is not about to be moved out of the screen (NO in step S28), the display-range setting circuit 116 sets a reduced image range to be displayed (step S32). In particular, when the display-range setting circuit 116 is the first display-range setting circuit 116*a*, the imaging apparatus 20 is instructed to narrow the field of view (extend the focal length). When the display-range setting circuit 116 is the second display-range setting circuit 116*b*, a to-be-displayed task image is generated for a narrow range.

The control circuit 100 transmits, to the display apparatus 30, the task image for which a display range has been changed in step S30 or S32, and the display apparatus 30 displays this task image.

The control circuit 100 decides whether the operator has performed an operation to acquire an image (step S34). The image acquisition in this situation means acquiring a still image as a task image. Upon deciding that the operator has performed an operation to acquire an image (YES in step S34), the control circuit 100 transmits an instruction to capture a still image to the imaging apparatus 20. Upon deciding that the operator has not performed an operation to acquire an image (NO in step S34), the control circuit 100 shifts to step S38.

Upon receipt of an instruction to capture a still image, the imaging apparatus 20 performs still-image capturing (YES in step T16). After performing still-image capturing, the imaging apparatus 20 transmits the captured still image to the task-image control apparatus 10 after associating this image with an image-capturing time (step T18). When the imaging apparatus 20 does not receive an instruction to capture a still image (NO in step T16), the imaging apparatus 20 returns to step T12.

The image acquisition circuit 102 acquires the transmitted still image (with the image-capturing time). The recording control circuit 140 records the still image and task step information in the evidence recording circuit 150 (step S36). The still image is recorded as image data 150*a*. The task step information is recorded as auxiliary data 150*c*. Sounds before and after the image-capturing timing of the still image may be recorded as sound data 150b.

The control circuit 100 decides whether the task has been ended (step S38). When, for example, an end button of an operation circuit (not illustrated) is pressed, the control circuit 100 decides that the task has been ended. Upon deciding that the task has not been ended (NO in step S38), the control circuit 100 returns to step S12. Upon deciding that the task has been ended (YES in step S38), the control circuit 100 ends the task process.

Second Embodiment

Figure 10:
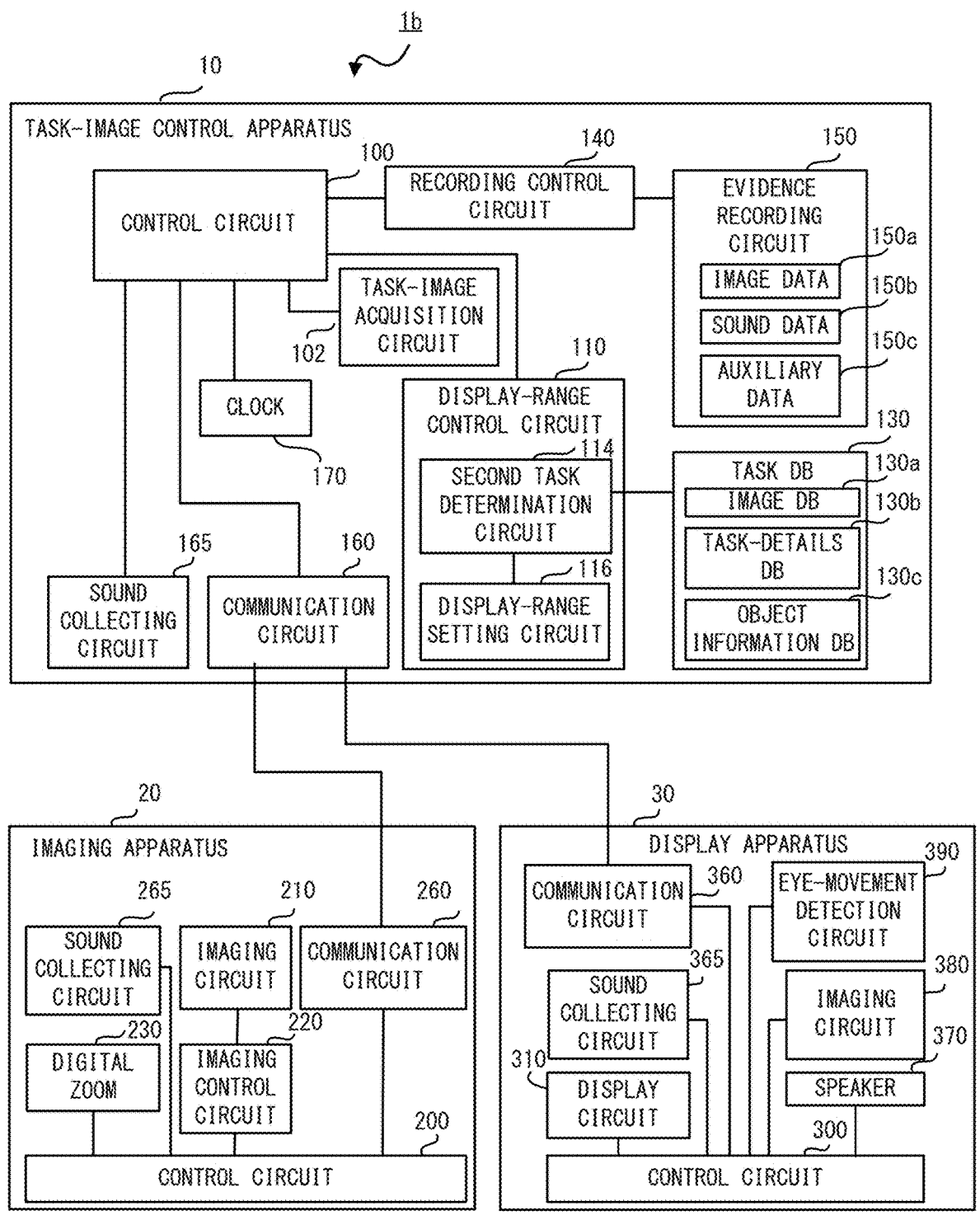
FIG. 10 is an entire configuration diagram of a task-image control system in accordance with a second embodiment.

FIG. 10 is an entire configuration diagram of a task-image control system 1b in accordance with a second embodiment. The task-image control system 1b is such that the operator watching a displayed task image is sensed and a portion focused on by the operator is decided to set a task-image range to be displayed in accordance with the operator's eye movement. The following mainly describes differences from the task-image control system 1 in accordance with the first embodiment.

The display apparatus 30 includes an imaging circuit 380 and an eye-movement detection circuit 390. The imaging circuit 380 is provided at an upper portion or a side portion of the display circuit 310 and captures an image of the operator's face (the eyes in particular) facing the display circuit 310. The eye-movement detection circuit 390 analyzes the orientation of the operator's face or the position of the pupil on the basis of the image captured by the imaging circuit 380 so as to detect the positions of portions of the task image displayed on the display apparatus 30 that are watched by the operator. The eye-movement detection circuit 390 transmits the detected positions of the watched portions of the task image to the task-image control apparatus 10 via the communication circuit 360.

The task-image control apparatus 10 includes a second task determination circuit 114 instead of the first task determination circuit 112. The second task determination circuit 114 calculates the distribution of the positions of the portions of the task image watched by the operator that have been detected on the display apparatus 30 and determines a focused-on portion of the task image on the basis of the distribution of the watched positions (also referred to as a watched-position distribution), thereby determining that the focused-on portion is a current task-target portion.

Figure 11:
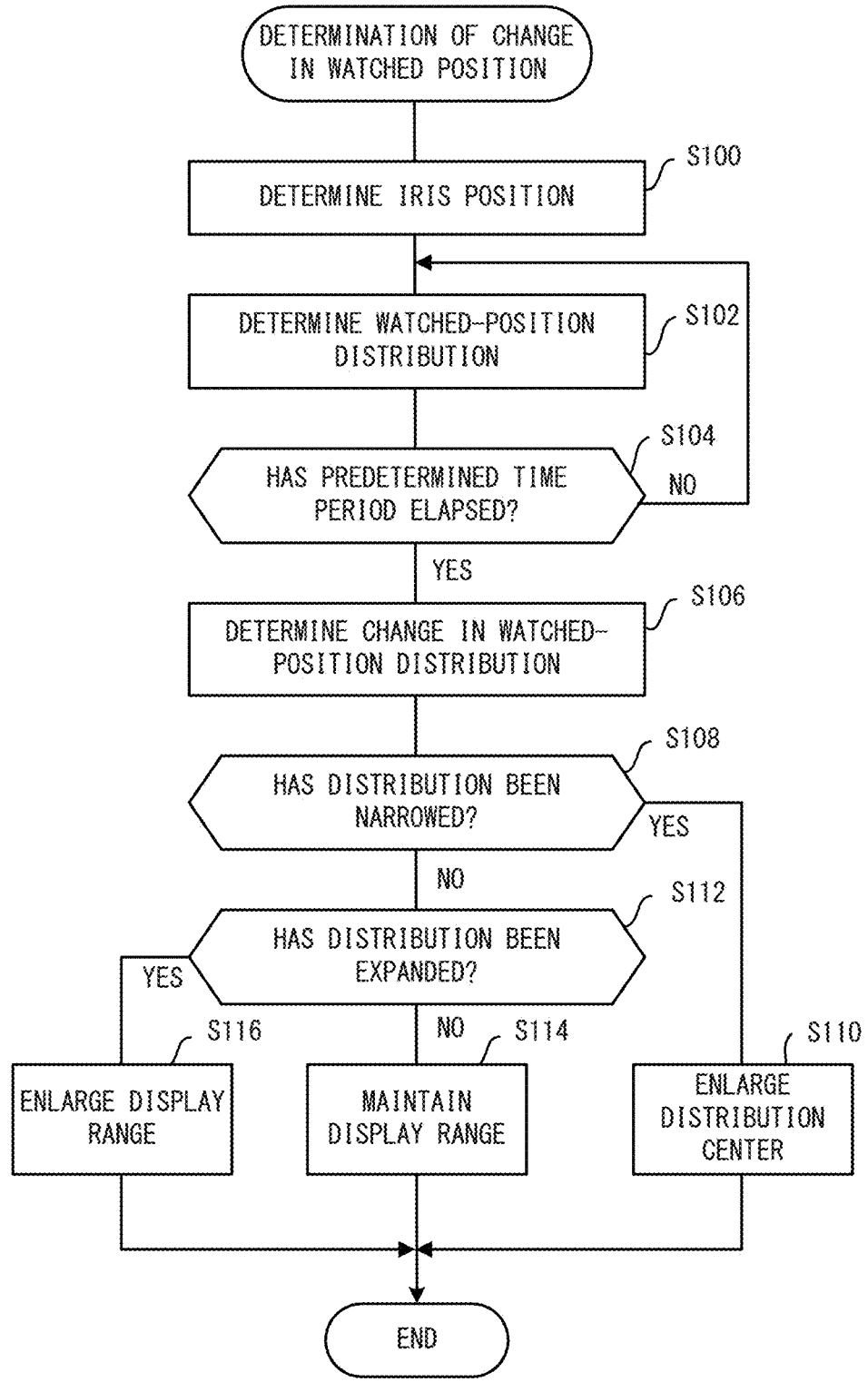
FIG. 11 is a flowchart illustrating the procedure of a process of determining whether a watched portion has been changed in accordance with a second embodiment.

FIG. 11 is a flowchart illustrating the procedure of a process of determining whether a watched portion has been changed. In the example described in the following, the display-range setting circuit 116 may be the first display-range setting circuit 116a or may be the second display-range setting circuit 116b.

The eye-movement detection circuit 390 determines the position of the operator's iris (step S100). The eye-movement detection circuit 390 determines the iris position by analyzing a face image of the operator captured by the imaging circuit 380. The eye-movement detection circuit 390 detects, on the basis of the determined iris position, the positions of portions of the image on the display circuit 310 that are watched by the operator and reports the detected positions to the task-image control apparatus 10. The second task determination circuit 114 determines a watched-position distribution on the basis of the reported watched positions (step S102).

The second task determination circuit 114 determines the distribution of watched positions detected within a predetermined time period (e.g., 10 seconds). The second task determination circuit 114 determines whether the predetermined time period has elapsed (step S104). Upon determining that the predetermined time period has not elapsed (NO in step S104), the second task determination circuit 114 returns to step S102.

Upon determining that the predetermined time period has elapsed (YES in step S104), the second task determination circuit 114 determines a change in the watched-position distribution (step S106). For example, the second task determination circuit 114 may determine a difference between a previous watched-position distribution and a current watched-position distribution.

The second task determination circuit 114 determines whether the watched-position distribution has been narrowed (step S108). Upon determining that the watched-position distribution has been narrowed (YES in step S108), the second task determination circuit 114 determines that the narrowed watched-position distribution is a task-target portion.

The display-range setting circuit 116 sets the narrowed watched-position distribution for a task-image range to be displayed. In particular, in the case of the first display-range setting circuit 116a, the imaging apparatus 20 is instructed to narrow the field of view in accordance with the narrowed watched-position distribution. The display apparatus 30 displays an image that corresponds to the narrowed watched-position distribution (enlarged image) (step S110). The enlarged image may be recorded by the task-image control apparatus 10 as an evidence image without being displayed on the display apparatus 30.

Upon determining that the watched-position distribution has not been narrowed (NO in step S108), the second task determination circuit 114 determines whether the watched-position distribution has been expanded (step S112). When the second task determination circuit 114 determines that the watched-position distribution has not been expanded (NO in step S112), the same display range is maintained (step S114).

When the second task determination circuit 114 determines that the watched-position distribution has been expanded (YES in step S112), the display-range setting circuit 116 makes a setting to expand the task-image range to be displayed. The display apparatus 30 displays an image of a wide range (step S116).

Figure 12B:
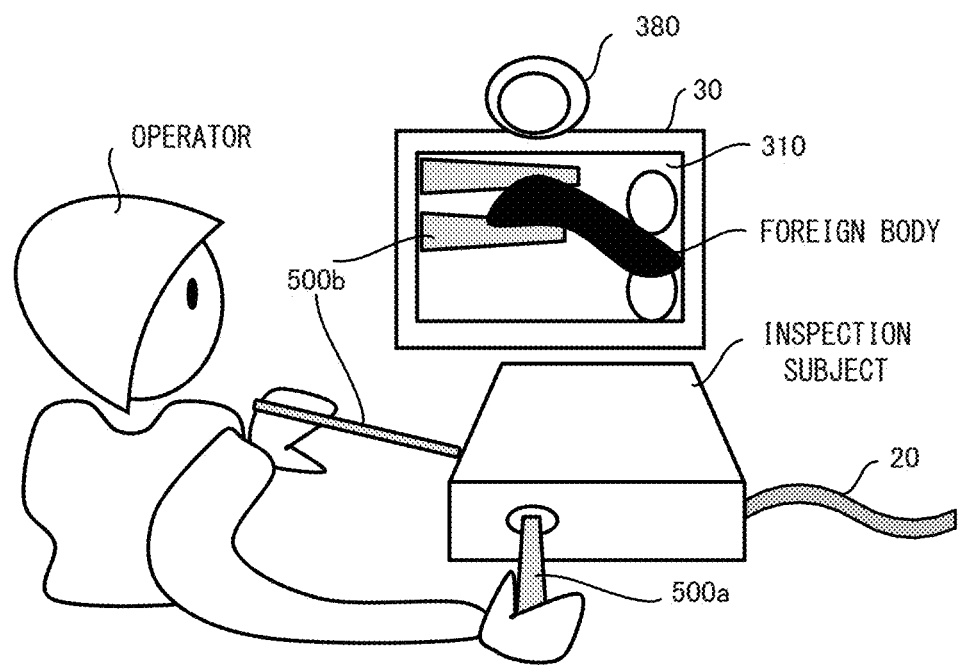
FIG. 12B illustrates an example of the switching of a display range in accordance with a second embodiment.

FIGS. 12A, 12B, and 13 each illustrate an example of the switching of a display range according to a change in a watched-position distribution. FIGS. 12A and 12B indicate how a task is performed. The operator performs a task of removing an internal foreign body by putting the cutter 500a and the pliers 500b into an inspection subject. A scope circuit of the imaging apparatus 20 is inserted into the inspection subject. The imaging circuit 380 is disposed at an upper portion of the display apparatus 30.

An image of the inside of the inspection subject that has been captured by the imaging apparatus 20 is displayed on the display circuit 310 of the display apparatus 30. The operator performs a task of grabbing the foreign body with the pliers 500b and cutting this foreign body with the cutter 500a while viewing the image displayed on the display apparatus 30.

FIG. 12A depicts a situation in which the operator performs a task of grabbing the foreign body with the pliers 500b. An image D20 depicted in FIG. 13 indicates watched positions E and a watched-position distribution (rectangular area indicated by a broken line) for the situation depicted in FIG. 12A. The points of the watched positions E indicate watched positions that have been detected. The watched positions E and the watched-position distribution indicated in FIG. 13 are presented merely for the sake of description and thus do not necessarily need to be displayed on the actual screen.

Image D20 indicates a situation in which the operator is bringing the pliers 500b close to the foreign body. The second task determination circuit 114 generates a diagram of the watched-position distribution (distribution 1) from the watched positions E. In the situation indicated by image D20, the operator advances the task while viewing various portions of the screen, and hence watched positions E are distributed throughout the screen.

Image D21 indicates a situation in which the operator has grabbed the foreign body with the pliers 500b. The second task determination circuit 114 generates a diagram of the watched-position distribution (distribution 2) from the watched positions E. In the situation indicated by image D21, the operator advances the task while focusing on the pliers 500b and the foreign body, and hence the distribution of watched positions E is concentrated on the pliers 500b and the foreign body and portions in the vicinity thereof.

The second task determination circuit 114 determines the distributions 1 and 2 (process of step S102) and determines a change between the distributions 1 and 2 (process of step S106). Then, the second task determination circuit 114 decides that the watched-position distribution has been narrowed (process of step S108), and the display-range setting circuit 116 displays an enlarged range of the distribution 2. FIG. 12B indicates the screen after the switching of the display range.

Third Embodiment

The descriptions have been given for the following task-determination schemes: the scheme for determining the type and movement of a tool and the scheme for identifying a task-target portion on the basis of the distribution of watched positions of the operator. Schemes for controlling a task-image range in accordance with task details are not limited to these and may include those based on machine learning. A third embodiment will be described hereinafter by referring to an example in which a task-image range to be displayed is controlled according to machine learning.

FIG. 14 is an entire configuration diagram of a task-image control system 1c in accordance with a third embodiment. The task-image control system 1c in accordance with the third embodiment corresponds to the task-image control system 1 in accordance with the first embodiment with the display-range control circuit 110 replaced with a machine learning circuit 120 and an inference model 122. The task-image control system 1c further includes an inference-model generation apparatus 400 that generates the inference model 122. The inference-model generation apparatus 400 is communicably connected to the task-image control apparatus 10. The inference-model generation apparatus 400 is, for example, a personal computer (PC). The components of the task-image control system 1c are the same as those of the task-image control system 1 in accordance with the first embodiment except for the machine learning circuit 120, the inference model 122, and the inference-model generation apparatus 400.

The inference-model generation apparatus 400 generates an inference model 122 (also referred to as a learning result) by learning a relationship between a past task image (referred to as, for example, a learning image or teacher data) and a task-image range to be displayed that corresponds to task details associated with the task image. The inference-model generation apparatus 400 transmits the inference model 122 to the task-image control apparatus 10. The task-image control apparatus 10 stores the received inference model 122 in, for example, the ROM 184.

On the basis of the generated inference model 122, the machine learning circuit 120 estimates a "task-image range to be displayed" that is recommended for task details associated with the task image. The control circuit 100 instructs the imaging apparatus 20 to change an image capturing range (field of view and direction) on the basis of the "task-image range to be displayed" estimated by the machine learning circuit 120. Alternatively, the control circuit 100 may extract the "task-image range to be displayed" estimated by the machine learning circuit 120 from the task image so as to generate a to-be-displayed task image. Processes performed after the estimation of the "task-image range to be displayed" are the same as those described above with reference to the display-range setting circuit 116 in accordance with the first embodiment, and detailed descriptions thereof are omitted herein.

The machine learning performed by the machine learning circuit 120 is implemented using a publicly known feature (technique), e.g., support vector machine (SVM), clustering, neural network, or decision tree learning.

Figure 15:
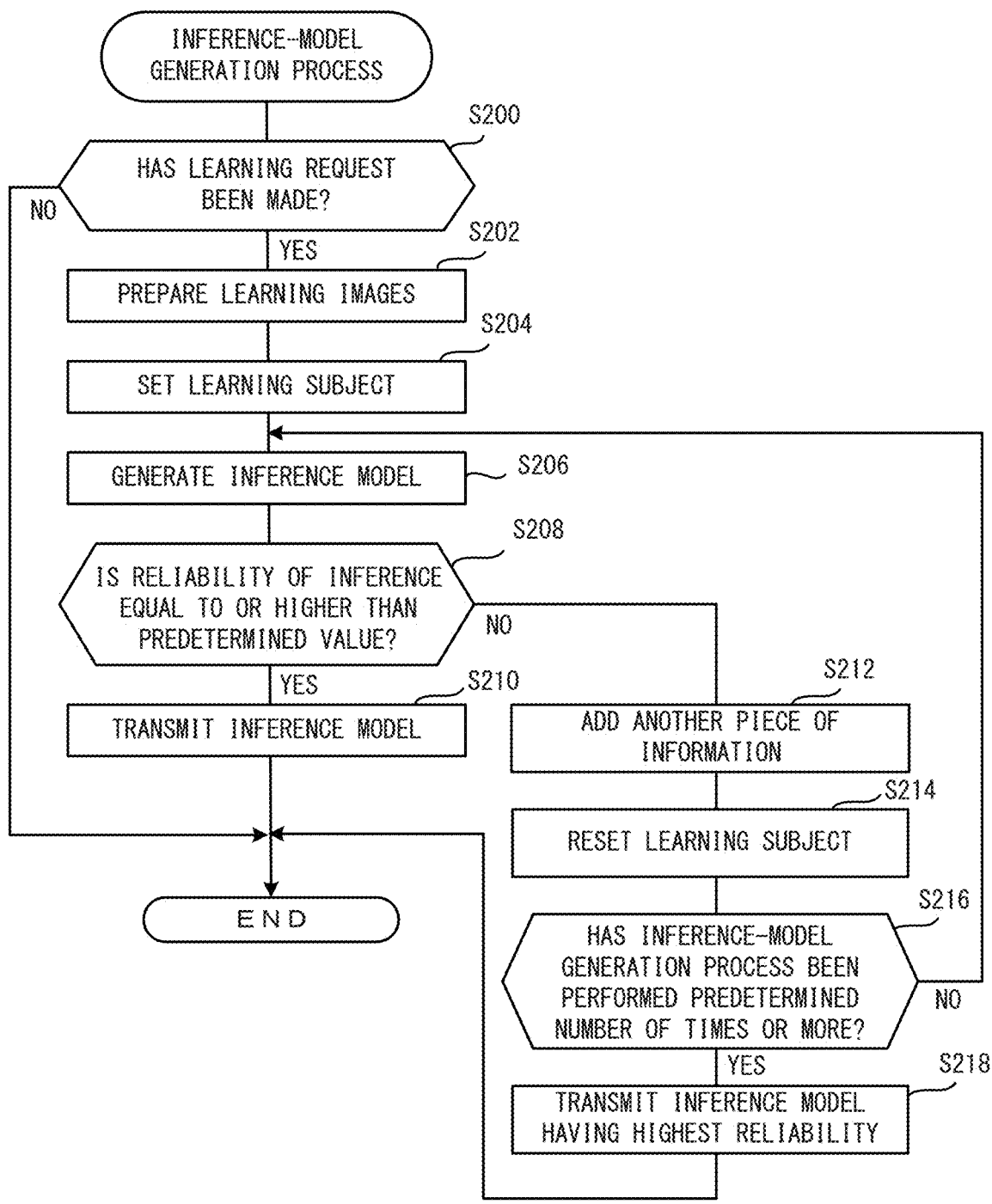
FIG. 15 is a flowchart illustrating a process of generating an inference model performed by a machine learning circuit in accordance with a third embodiment.

FIG. 15 is a flowchart illustrating a process of generating the inference model 122. The inference model 122 is generated by the inference-model generation apparatus 400. The inference-model generation apparatus 400 determines whether an administrator or the like has made a learning request (step S200). Upon determining that a learning request has not been made (NO in step S200), the inference-model generation apparatus 400 ends this process.

Upon determining that a learning request has been made (YES in step S200), the inference-model generation apparatus 400 prepares various task images (preferably having a tool indicated therein) as learning images (also referred to as teacher data) (step S202). The task images are each associated with field-of-view data serving as an imaging parameter or with information on a range to be displayed or recorded in a prioritized manner.

The inference-model generation apparatus 400 sets a learning subject from among the prepared learning images on an as-needed basis (step S204). In this case, information on a task-image range may be manually input to the teacher data. Information on the positions of portions watched by the operator (FIG. 13) may be manually input to the teacher data. Alternatively, the inference-model generation apparatus 400 may such that information on a task-image range may be manually set for some pieces of teacher data and then information on the position of a portion watched by the operator may be used as a portion of the teacher data.

The model for which learning has been performed as described above, i.e., a learning-completed model (inference model), determines task details on the basis of the type of a tool detected within a task image or the position of the portion watched by the operator, so that task assistance such as message displaying, guide, and evidence acquisition can be given to the operator without troublesome operations being performed by the operator during the task.

Not only images but also information on the position of a portion watched by the operator during a task may be input to allow the inference-model generation apparatus 400 to perform an inferring operation. The inference-model generation apparatus 400 may perform a learning process in consideration of the movement of a tool.

Figure 16:
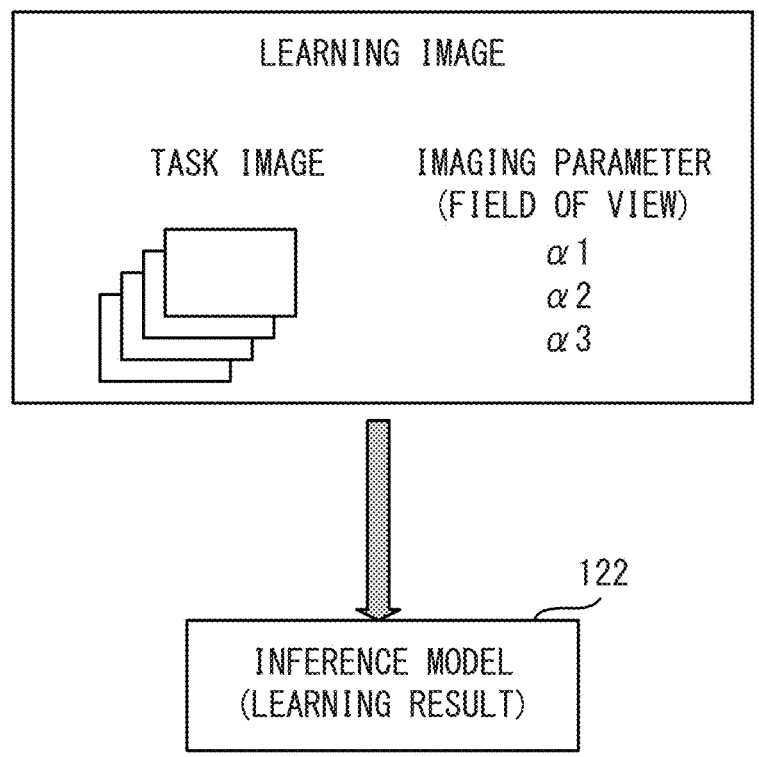
FIG. 16 schematizes the generation of an inference model in accordance with a third embodiment.

The inference-model generation apparatus 400 performs a learning process to generate an inference model 122 (step S206) (see FIG. 16).

The inference-model generation apparatus 400 determines whether the inference model 122 has a reliability of a predetermined value or higher (step S208). Upon determining that the reliability of the inference model 122 is equal to or higher than the predetermined value (YES in step S208), the inference-model generation apparatus 400 transmits the inference model 122 to the task-image control apparatus 10 (step S210). The inference model 122 is stored in, for example, the ROM 184 of the task-image control apparatus 10.

Upon determining that the reliability of the inference model 122 is not equal to or higher than the predetermined value (NO in step S208), the inference-model generation apparatus 400 adds another piece of information to the learning images (step S212) or resets the learning subject (step S214).

The inference-model generation apparatus 400 decides whether the inference-model generation process has been performed a predetermined number of times or more (step S216). Upon deciding that the inference-model generation process has not been performed the predetermined number of times or more (NO in step S216), the inference-model generation apparatus 400 returns to step S206 and performs the inference-model generation process again.

Upon deciding that the inference-model generation process has been performed the predetermined number of times or more (YES in step S216), the inference-model generation apparatus 400 transmits an inference model 122 having the highest reliability among the inference models 122 generated up to this moment to the task-image control apparatus 10 (step S218). Then, the inference-model generation process is ended.

FIG. 17 models processing performed by the machine learning circuit 120. The machine learning circuit 120 includes, for example, a neural network having a multilayer structure provided with an input layer, an intermediate layer, and an output layer. The machine learning circuit 120 inputs a task image captured by the imaging apparatus 20 to a generated inference model 122 and acquires, for example, a field of view as an output.

The machine learning circuit 120 may be applied to the display-range control circuit 110 in accordance with the second embodiment. In this case, the inference-model generation apparatus 400 generates, as an inference model 122, a model for estimating a field of view and an image capturing direction for a task image from the state of a watched-portion distribution of the operator. Inputting the watched-portion distribution of the operator to the inference model 122 allows the machine learning circuit 120 to obtain a field of view and an image capturing direction that are to be set for a task image. By learning such factors as described above, an important image range can be inferred by inputting a captured image alone or can be inferred by inputting a captured image and the orientation of the operator's eye.

Accordingly, the task-image control system is such that the range and size of a displayed task image are automatically switched to those suitable for task details in accordance with the progress of a task, so that the operator can concentrate on the task without the hassle of manipulating the imaging apparatus (camera).

The task-image control system 1 in accordance with the first embodiment changes a displayed task-image range in accordance with the type or movement of a tool and thus displays a range that depends on task details. The task-image control system 1b in accordance with the second embodiment changes a displayed task-image range in accordance with a watched-portion distribution of the operator and thus appropriately changes a display range even in a task in which tools are switched only a few times.

According to the descriptions given so far, the control circuit 100 and display-range control circuit 110 of the task-image control apparatus are implemented through software processing performed by a CPU that has read a program. However, portions of or the entirety of the control circuit 100 and the display-range control circuit 110 may be implemented by hardware such as a gate array.

At least portions of or the entirety of each component described as a "circuit" with reference to the embodiments herein may be a combination of a dedicated circuit and a plurality of general-purpose circuits or may be, as appropriate, a combination of microcomputers, processors (e.g., CPUs) that run in accordance with software programmed in advance, or sequencers (e.g., FPGAs). For example, the control circuit 100, task-image acquisition circuit 102, display-range control circuit 110, first task determination circuit 112, second task determination circuit 114, display-range setting circuit 116, first display-range setting circuit 116a, second display-range setting circuit 116b, manipulator guide circuit 116c, machine learning circuit 120, recording control circuit 140, communication circuit 160, and sound collecting circuit 165 of the task-image control apparatus 10 may be discrete circuits, may be circuits partly or entirely integral with each other, or may be partly or entirely implemented by a processor that runs in accordance with software programmed in advance. Meanwhile, the control circuit 200, imaging circuit 210, imaging control circuit 220, digital-zoom processing circuit 230, communication circuit 260, and sound collecting circuit 265 of the imaging apparatus 20 may be discrete circuits, may be circuits partly or entirely integral with each other, or may be partly or entirely implemented by a processor that runs in accordance with software programmed in advance. In addition, the control circuit 300, display circuit 310, communication circuit 360, sound collecting circuit 365, speaker 370, imaging circuit 380, and eye-movement detection circuit 390 of the display apparatus 30 may be discrete circuits, may be circuits partly or entirely integral with each other, or may be partly or entirely implemented by a processor that runs in accordance with software programmed in advance.

A possible design is such that portions of or the entirety of the control is performed by an external apparatus, and in this case, a wired or wireless communication circuit is provided. A communication may be performed via Bluetooth®, WiFi, or a telephone line or via USB. A dedicated circuit, a general-purpose circuit, and a control circuit may be integrated as an ASIC.

The lens driving circuit includes various actuators and also includes, as appropriate, a coupling mechanism for movement, wherein the actuators are operated by a driver circuit. The driver circuit is also controlled by a microcomputer, an ASIC, or the like in accordance with a certain program. According to such a control operation, precise corrections and adjustments may be made in accordance with information output from various sensors or circuits located in the vicinity of these sensors. A plurality of apparatuses and devices cooperate to provide certain functions. Accordingly, functions of one of these devices may be achieved by another, and a possible improvement is such that an additional device is provided as a substitute to implement a necessary function.

The embodiments described above provide a task-assistance control apparatus capable of displaying an image appropriate for task details.

The present invention is not limited to the described embodiments and may be achieved in an implementation phase with components modified without departing from the gist of the invention. Various inventions may be provided by combining, as appropriate, a plurality of components disclosed with reference to the embodiments. For example, all components indicated with reference to an embodiment may be combined as appropriate. Moreover, components of different embodiments may be combined as appropriate. Needless to say, various modifications and applications can be provided in this way without departing the gist of the invention.

The invention claimed is:

1. A task-image control apparatus that assists an operator performing a task while viewing a captured task image, the task-image control apparatus comprising:
   a task determination circuit that determines task details on the basis of the task image; and
   a display-range setting circuit that sets, in accordance with the determined task details, a task-image range to be displayed, wherein
   the task determination circuit detects a type of a tool used for the task from the task image and determines task details in accordance with the type of the tool; and
   the task determination circuit compares the type of the tool detected from the task image with types of tools scheduled to be used in various steps of the task so as to determine a task step that corresponds to the task image.

2. A task-image control apparatus that assists an operator performing a task while viewing a captured task image, the task-image control apparatus comprising:
   a task determination circuit that determines task details on the basis of the task image; and
   a display-range setting circuit that sets, in accordance with the determined task details, a task-image range to be displayed, wherein
   the task determination circuit calculates a distribution of portions watched by the operator that have been detected within a predetermined time period, and determines a portion focused on by the operator on the basis of a change in a watched-portion distribution.

* * * * *